United States Patent

Gust

[11] Patent Number: 5,828,454
[45] Date of Patent: Oct. 27, 1998

[54] OPTICAL HETERODYNE INTERFEROMETER FOR MEASUREMENT OF OCULAR DISPLACEMENT

[76] Inventor: Gary R. Gust, 16391 Maruffa Cir., Huntington Beach, Calif. 92649

[21] Appl. No.: 681,804

[22] Filed: Jul. 29, 1996

[51] Int. Cl.$^6$ .................................................. G01B 9/02
[52] U.S. Cl. ............................... 356/349; 351/212; 606/4
[58] Field of Search ..................................... 356/345, 349, 356/359, 360, 357, 358; 351/212, 221, 205, 211; 128/633

[56] References Cited

U.S. PATENT DOCUMENTS

| | | |
|---|---|---|
| 3,948,248 | 4/1976 | Zuckerman et al. . |
| 4,834,111 | 5/1989 | Khanna et al. ......................... 356/351 |
| 4,928,697 | 5/1990 | Hsu . |
| 5,148,807 | 9/1992 | Hsu . |

OTHER PUBLICATIONS

Electro–Optics Consultants, Inc., "Final Report—Cornea Optical Topographical Scan System (COTSS))", Submitted to: National Aeronautics and Space Administration Marshall Space Flight Center, AL 35812, Dec. 31, 1988.

Kasprzak, Henry K.; Foster, Werner; Von Bally, Gert, "Measurement of Elastic Modulus of the Bovine Cornea by Means of Holographic Interferometry. Part 1. Method and Equipment", Optometry and Vision Science, American Academy of Optometry, vol. 70, No. 7, pp. 535–444, May 14, 1992.

Hamelink, J.M.; Cloud, G.L., "Ocular Tonometry Through Sonic Excitation and Laser Doppler Velocimetry", Transactions of the ASME, vol. 101, pp. 267–270, Nov. 1979.

Crane, Robert, "Interference Phase Measurement", Applied Optics, vol. 8, No. 3, pp. 538–542, Mar. 1960.

Massie, N.A.; Nelson, R.D.; and Holly, S., "High–Performance Real–Time Heterodyne Interferometry", Applied Optics, vol. 18, No. 11, pp. 1797–1803.

Hastings, M.C.; Roberts, C.; and Barr, J.T., "Assessment of Mechanical Properties of the Cornea as a Function of Changes in Structure of Pathology", Investigative Ophthalmology & Visual Science, vol. 37, No. 3, Feb. 15, 1996.

*Primary Examiner*—Samuel A. Turner
*Attorney, Agent, or Firm*—Bromberg & Sunstein LLP

[57] ABSTRACT

A method and apparatus for non-contact measurement of the precise displacement, movement, and mechanical properties of an eyeball. An optical heterodyne interferometer is provided having a measurement beam and a reference beam. A modulator shifts the frequency of the reference beam. The measurement beam, after reflection from the eyeball, is combined with the reference beam on a heterodyne detector and the relative phase of the reflected beam and reference beam is measured and the ocular displacement is calculated so that physiological properties may be determined.

34 Claims, 4 Drawing Sheets

OPTICAL HETERODYNE INTERFEROMETER FOR MEASUREMENT OF OCULAR DISPLACEMENT

BACKGROUND OF THE INVENTION

The present invention relates to an optical heterodyne interferometer for non-contact measurement of the topography and mechanical properties of the eye and for application in deriving other physiological properties.

Measurement of the displacement of the eyeball has many diagnostic applications in both clinical and research settings. In some regards, measurement of the displacement provides all the information which can be derived from measurement of ocular pressure in that internal pressure may be derived from a measurement of the displacement of the cornea in response to an applied force. Some of the applications include:

a. Assessment of changes in corneal structure due to healing after injury or surgery, and diagnosis and management of pathology, based on local mechanical properties such as corneal stiffness or Young's modulus of elasticity. This information is critically useful, for example, for improved results in refractive correction surgery.

b. Ocular blood flow measurements and other ocular or cardiovascular diagnostics which require measurement of the ocular pulse, since the fine structure of the ocular pulse reflects the spatial distribution of ocular blood flow which derives from the internal carotid artery. The bifurcation of the internal and external carotid arteries is prone to vascular occlusion.

c. Measurement of ocular pressure as a clinical manifestation of glaucomatous symptoms which, untreated, lead to impaired vision and, ultimately, blindness.

An entire class of instruments historically and currently employed for the measurement of ocular properties require physical contact of the instruments with the eyeball. One example of this class of instruments includes placing a calibrated piezoelectric weight on the anesthetized corneal surface. Another example is the opthalmodynamometer which is held manually against the eyeball with a plunger exerting a force on the eyeball to achieve a specified applanation of the cornea. The opthalmodynamometer then measures the countervailing force to derive systolic and diastolic ocular pressure. For measurement of pressure alone, air puff systems have been employed which deform the local surface shape of the cornea as it is concurrently monitored optically. In a clinical setting, all of the contact and air puff methods are uncomfortable to the patient. The contact methods additionally require specialized skill and subjective judgment on the part of the practitioner, and incur the risk of infecting or abrading the cornea.

The method taught by the present invention is practiced without physically contacting the eye, and the apparatus for practicing it offers several advantages over other non-contact methods of monitoring the eyeball which allow it to provide greater sensitivity and accuracy in a clinical context. One of the non-contact methods known in the art entails monitoring the reflection of ultrasonic waves from the eye for changes in frequency due to motion of the reflecting surface.(Zuckerman et al., U.S. Pat. No. 3,948,248) Additionally, ultrasound reflection from the eyeball may be modulated in response to an excitation of the eyeball by low frequency sound. (Hsu, U.S. Pat. No. 4,928,697). The application of the ultrasound reflection method to enucleated bovine eyes has been reported in the abstract of "Assessment of Mechanical Properties of the Cornea as a Function of Changes in Structure or Pathology, " by Hastings et al., *Investigative Opthalmology & Visual Science,* 37:S314 (1996). The amplitude and phase of the corneal motion can be obtained in this manner.

Another non-contact method known in the art employs laser Doppler velocimetry in which an acoustic wave and an optical probe are directed toward the surface of the eye, causing the reflected light to be shifted slightly in frequency due to the velocity at which the cornea responds to its acoustic excitation. This technique, however, fails to allow study of the static displacement of the eye surface.

Other optical methods are interferometric, as discussed, for example, in "Measurement of Elastic Modulus of the Bovine Cornea by Means of Holographic Interferometry," by Kasprzak, et al., *Optometry and Vision Science,* 70:535 (1993) and in Hsu (U.S. Pat. No. 5,148,807). In interferometry, the phase of an optical or ultrasound wave reflected by the eyeball is detected and may be mapped across some portion of the surface of the eye. Interferometric methods hitherto known in the art look at excursions of interference fringes about some static reference. In other words, their sensitivity is limited to detection of movement, and that detection is performed, in frequency space, about zero frequency, where phase noise is greatest.

The technique taught by this invention monitors not only corneal motion but also allows for the static monitoring of corneal position. Additionally, it provides improved sensitivity to corneal displacement. A vast improvement in sensitivity and immunity to low frequency noise is obtained by means of heterodyning the reflection from the eye with a frequency-shifted coherent reference. This allows the absolute static position of a point on the corneal surface to be monitored in real time. Thus, low frequency perturbations causing minute motions of the surface, such as induced by the ocular pulse, are readily resolved using a non-contact means. Additionally, it is possible to apply an external perturbation in the form of a sound wave coaxial with the optical probe beam, and to measure the time-resolved response of the corneal surface. Mechanical properties of the surface can thus be derived. While the eye is apt to wander so that an acoustic excitation will not remain aimed at the corneal apex as originally positioned, the invention further ensures the precise orthogonality of any acoustic excitation to the tangent to the surface of the eye. This resolves a calibration ambiguity present in previous methods.

SUMMARY OF THE INVENTION

In accordance with the present invention, in one embodiment, there is provided an optical heterodyne interferometer for measuring precise displacement, movement, and mechanical properties of an eyeball, having a modulator for shifting the frequency of at least one of a measurement beam and a reference beam, while an optical configuration steers the measurement beam onto the surface of the eyeball. The beam reflected from the eyeball is combined with the reference beam on a heterodyne detector. The invention also has a phase detector for detecting the relative phase of the reflected beam with respect to the reference beam and a signal processor for calculating ocular displacement. In a further embodiment, there is provided a method for measuring the intraocular pressure of an eyeball.

The ocular optical heterodyne interferometer described herein advantageously provides the capability of measuring displacements of the front surface of an eyeball to extremely high accuracy. Additionally, it provides improved reliability of calibration, simplicity of use, and is free of the effect of subjective judgment on the acquisition and interpretation of the data. This invention further ensures that the precise apex of the eyeball is sampled, with an accuracy and calibration that do not rely upon critical alignment with the eye or the shape of the eye. This invention also provides for determining continuous intraocular pressure for the purpose of other diagnostic tests such as blood flow analysis and additional tests which may become useful by virtue of the increased sensitivity of this instrument.

Other objects and advantages of the invention are in part apparent and in part pointed out hereinafter.

DETAILED DESCRIPTION OF THE PREFERRED EMBODIMENTS

Figure 1:
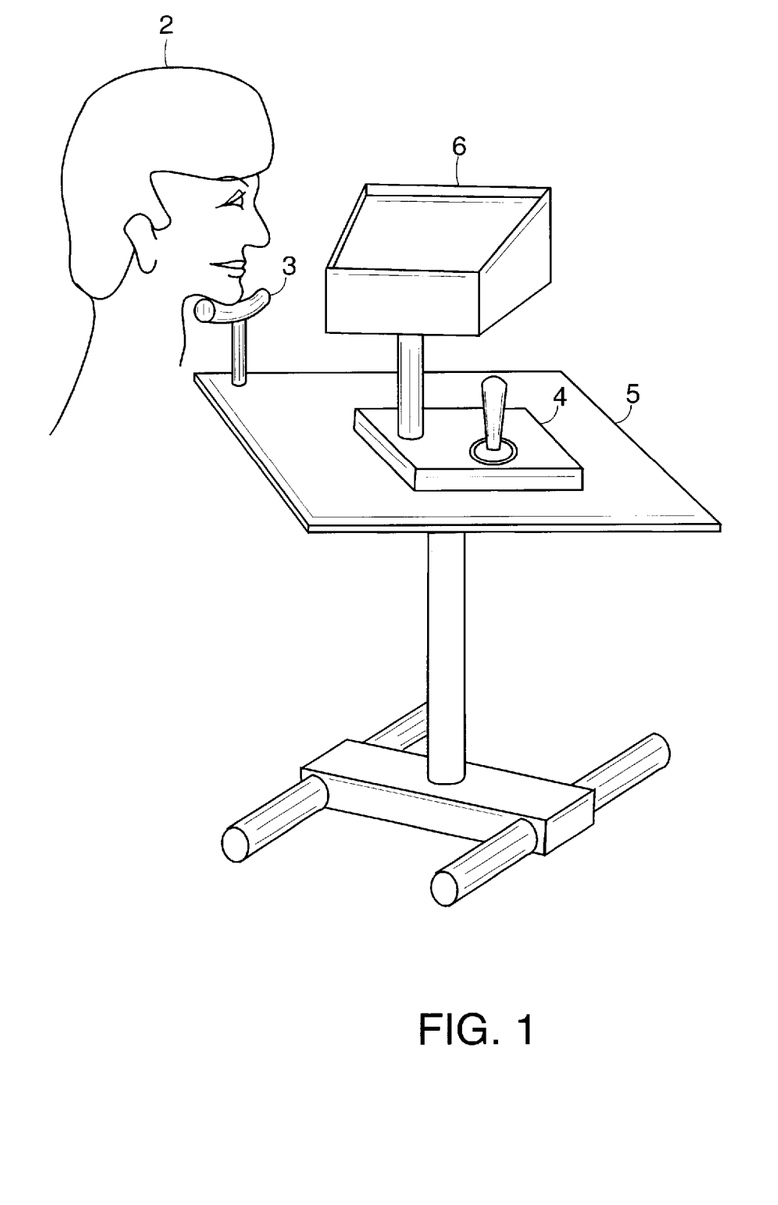
FIG. 1 is schematic view of the mechanical layout of the current invention.

The features of the ocular optical heterodyne interferometer are now described with reference to FIG. 1, wherein the interferometer is indicated by reference character 6. The preferred embodiment, referred to as a console type instrument and indicated generally by reference character 1, is employed in a clinical context, where the subject is a human patient (not shown). Headrest 3 is used to hold the patient's head 2 in a stationary position with respect to interferometer 6. Adjustable table 5 provides adjustability of headrest 3 so that patient's head 2 rests motionless and comfortably in headrest 3. Interferometer 6, in turn, is attached via adjustable base 4 to adjustable table 5 such that interferometer 6 can be moved in three degrees of freedom for alignment with respect to the patient's eyeball (not shown).

Figure 2:
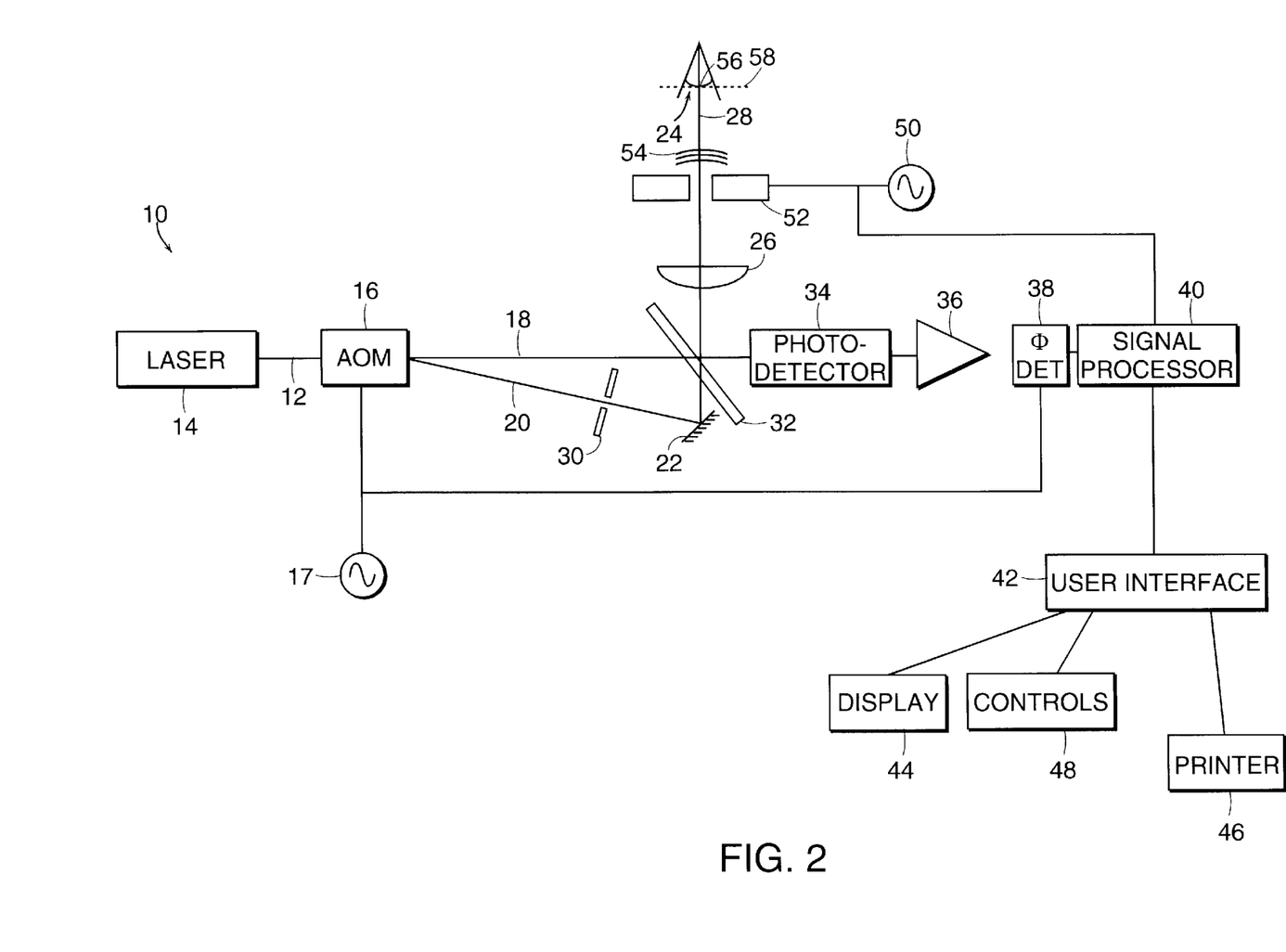
FIG. 2 is schematic view of the operation of the current invention.

The operational features of the ocular optical heterodyne interferometer 6 are now described with reference to FIG. 2, wherein the interferometer is indicated generally by reference character 10. In the preferred embodiment, coherent light beam 12 is emitted by coherent light source 14, which, by way of example, may be a He-Ne laser operating at a wavelength of 632.8 nanometers, however the precise wavelength of the light and its means of generation are matters of design choice.

Light beam 12 is divided into two beams: reference beam 18 and measurement beam 20. In the preferred embodiment, the division occurs at modulator 16, which, in the preferred embodiment, is an acoustooptic modulator. Alternatively, light beam 12 can be divided into reference beam 18 and measurement beam 20 using other forms of beam splitters well known in the art. Other optical designs are also known in the art by means of which coherent light beams may be provided externally to serve as reference beam 18 and measurement beam 20. Modulator 16 serves to shift the frequency of reference beam 18 by superposing a radio-frequency modulation, the frequency of which is a matter of design choice. Alternatively, measurement beam 20 may be shifted in frequency, instead of, or in addition to, reference beam 18. In the best mode, a modulation frequency of approximately 70 MHZ is used, as determined by the frequency output of frequency generator 17 which drives modulator 16. It is to be understood that the best mode employs acoustooptic modulation for shifting the frequency of reference beam 18, but that other modulation mechanisms known in the art are also within the scope of the invention.

Measurement beam 20 is directed toward eyeball 24 of the subject (not shown) by an optical means, represented in one embodiment by mirror 22 and lens 26. While mirror 22 is merely illustrative of a beam-steering arrangement, of which many are readily configured by a person skilled in the optical arts, it is important to the operation of the invention that the f-number of lensed measurement beam 28, incident on eyeball 24, be large in order both to ease the criticality of clinical alignment and to provide a tolerance of interferometer 6 to involuntary motions of eyeball 24 in the lateral directions of lensed measurement beam 28. In the best mode, lens 26 has a focal length of 200 mm, while aperture 30 is provided at the field stop of measurement beam 20 to provide a typical f-number on the order of several hundred.

The means of splitting light beam 12 into reference beam 18 and measurement beam 20 ensures that a safe level of light power in measurement beam 20 is incident on eyeball 24. Alternatively, beam attenuation means well known in the art, such as neutral density filters (not shown) may be used. In the preferred embodiment, the output power of coherent light source 14 is approximately 2 milliwatts, while, typically, on the order of half a microwatt of light power is incident on eyeball 24.

After reflection back from eyeball 24, lensed measurement beam 28 is recombined with reference beam 18 in such a manner that lensed measurement beam 28 and reference beam 18 fall onto heterodyne detector 34 with substantially overlapping wavefronts (not shown). By way of example, the beam recombination means may be a beam splitter 32, but other arrangements are known to persons skilled in the optical arts for combination of two beams and the invention may be practiced using those arrangements as well. Heterodyne detector 34 may be any square-law optical detector which is sensitive to the modulus of the incident electromagnetic field due to the coincident detection of lensed measurement beam 28 and reference beam 18. In the preferred embodiment, heterodyne detector 34 is a photodiode. Heterodyne detector 34 must provide sufficient bandwidth for heterodyne recovery of the modulation frequency impressed on reference beam 18 by modulator, which, in the preferred embodiment, is approximately 70 MHZ. The resultant heterodyne signal contains the modulation frequency of 70 MHZ and also modulation due to motion of apex 56 of eyeball 24. The phase of the heterodyne signal with respect to the output of frequency generator 17 depends on the displacement of eyeball 24. The heterodyne signal output of heterodyne detector 34 is amplified by preamplifier 36. The bandpass of preamplifier 36 is centered about the frequency of frequency generator 17 and has sufficient bandwidth to pass modulation due to changes in the displacement of eyeball 24. Because of the phenomenon of heterodyne interferometry, the phase difference between the heterodyne signal and the output of frequency generator 17 represents the optical path length difference between the two optical paths taken by the two beams, reference beam 18 and measurement beam 20.

Phase detector 38 receives the heterodyne signal as amplified by preamplifier 36, and mixes the heterodyne signal with the output of frequency generator 17 to derive low frequency signals which contain information regarding the displacement and motion of eyeball 24. A phase detector produces a single signal wave each time the surface under test moves a distance equivalent to the wavelength of the light used in the interferometer. Commonly known phase detectors are able to resolve $\frac{1}{300}$ or less of a full wave in phase. Since the wavelength of coherent light source 14, in the preferred embodiment, is 633 nanometers, the method taught here is capable of measuring the displacement of the surface of eyeball 24 to a resolution of about 2 nanometers. The operation of phase detector 38 is discussed below in greater detail.

The low frequency signal output of phase detector 38, containing information regarding the displacement and motion of eyeball 24, is digitized and analyzed by signal processor 40. Displacement information is provided to the user via user interface 42. Since analysis of the relative phase provides the displacement of eyeball 24 directly, no Fourier transformation is required as in other interferometric techniques. In particular, a time record of eyeball displacement may be provided to the user via display 44, which, in the preferred embodiment is a video monitor, or printed on printer 46. The various embodiments of a user interface 42, its display 44 and control system 48, are well known to persons skilled in the art.

The measurement of various ocular properties such as ocular pressure and corneal elasticity can be accomplished through acoustic excitation of eyeball 24 and measurement of the resulting displacement of eyeball 24 using the method which has been described. To provide acoustic excitation, an audio frequency generator 50 drives an acoustic generator 52 which directs a roughly planar, uniform sound wave 54, of frequency typically between 10 and 500 Hz, onto eyeball 24. Arrangement of acoustic generator 50 coaxially disposed with respect to lensed measurement beam 28, such that sound wave 54 impinges on eyeball 24, insures that lensed measurement beam 28 and sound wave 54 are precisely coincident at eyeball 24.

For a measurement of ocular pressure, the strength of sound wave 54 is maintained stable over long periods of time. Sound wave 54 is also substantially uniform in strength over the tolerance in distance between interferometer 10 and eyeball 24 such that the sound pressure on eyeball 24 does not change within clinically required tolerances as interferometer 10 is aligned with respect to eyeball 24, or, alternatively, the dependence on distance is known and accounted for to within required tolerances.

When an optical heterodyne measurement of displacement is made using the invention in conjunction with acoustic excitation, such as for tonometry, the output of audio frequency generator 50, which drives acoustic generator 52, is supplied to signal processor 40 which is then able to apply common synchronous signal processing techniques to derive quantities including the amplitude and peak-to-peak distance of the response of eyeball 24 to acoustic excitation. Synchronous signal processing isolates the motion amplitude due solely to the acoustic excitation and therefore discriminates against all other motion due to acoustic noise in the environment or physiological motions. Methods for calibrating the intensity of sound wave 54 at the corneal surface are well known to persons skilled in the art. Intraocular pressure may thus be derived from the amplitude of vibration of the surface of eyeball 24, synchronous with the acoustic excitation provided by acoustic generator 52. In the preferred embodiment, an empirical clinical calibration is performed by fitting the measured amplitude of vibration in response to acoustic excitation against intraocular pressure derived in a clinical sample by means of an accepted alternate methodology. The fit is performed assuming an inverse functional relationship between intraocular pressure and amplitude of vibration, with a multiplicative constant determined by empirical study of a clinical sample. Other functional relationships may also be fit, and, alternatively, the fit may remain unconstrained by a model.

Since operation of interferometer 10 requires the coincidence at heterodyne detector 34 of the wavefronts of measurement beam 20 and reference beam 18, detection of a heterodyne signal ensures that lensed measurement beam 28 is being reflected substantially back on itself. This, in turn, ensures that both lensed measurement beam 28 and sound wave 54, which are collimated by design, are incident on the surface of eyeball 24 at a probe point 56 such that a plane 58 tangent to the surface of eyeball 24 at probe point 56 is perpendicular to the bisector of the angle between incident lensed measurement beam 28 and its reflection from eyeball 24. Thus, probe point 56 constitutes the apex of eyeball 24. This feature of the invention assures accuracy of calibration since, by design, any component of sound wave 54 which is tangent to eyeball 24 is minimized and thus does not contribute significantly to the compressive diagnostic force. Signal processor 40 may thus be programmed, employing standard programming techniques, to ensure that data are taken only when the described conditions of normal incidence obtain. Furthermore, in an alternative embodiment of the invention, a control signal is provided by signal processor 40 to actively control the optical means, represented, in the embodiment shown, by mirror 22 and lens 26, for directing measurement beam 20 toward eyeball 24 to track movement of eyeball 24. Any of the means of compensatory tracking of eyeball movement which are well known in the art may be employed for this purpose.

Figure 3:
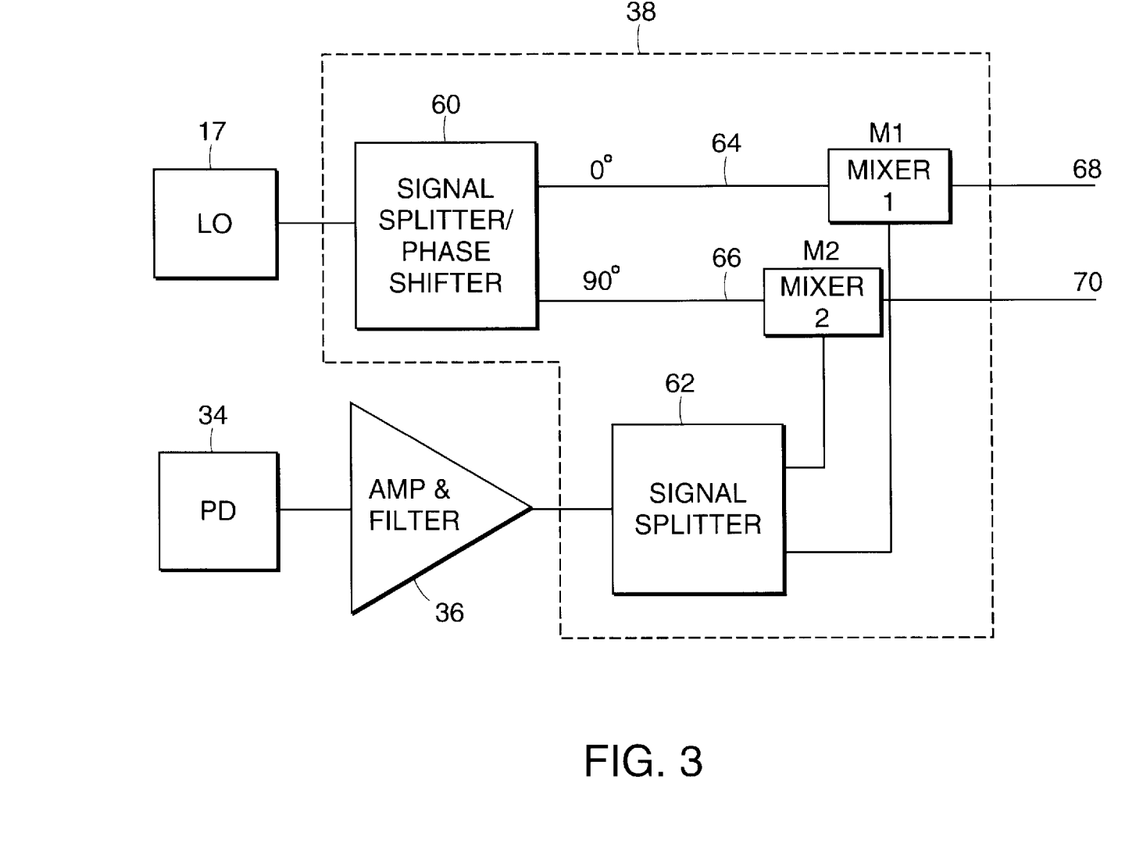
FIG. 3 is a block diagram of the post-detection electronics of the current invention.

The operation of phase detector 38 in the preferred embodiment is now described with reference to FIG. 3. Phase detector 38 is shown to include a phase shifter 60, a signal splitter 62, and mixers M1 and M2. Phase shifter 60 receives the radio frequency output of frequency generator 17 and provides outputs 64 and 66 which are shifted in phase, respectively, by 0° and 90°. The heterodyne signal output of heterodyne detector 34, amplified by preamplifier 36, is split by signal splitter 62, and mixed with the unshifted output 64 of frequency generator 17 in mixer M1, and with the 90°-shifted output 66 of frequency generator 17 in mixer M2. The outputs of mixers M1 and M2, designated, respectively, by numerals 68 and 70, represent the cosine 68 and sine 70 of the phase shift between the output of heterodyne detector 34 and frequency generator 17. Since both cosine 68 and sine 70 outputs are available, the phase, including both magnitude and sign, are available to signal processor 40. In an alternative embodiment, only a single phase is processed, with possible loss of direction information, or, in further alternative embodiments, the heterodyne signal output of heterodyne detector 34, amplified by preamplifier 36, is split by signal splitter 62, and mixed with a plurality of phase shifted copies of the output of frequency generator 17. Cosine 68 and sine 70 outputs are amplified and low-pass filtered with a cutoff of typically 10 kHz, and AC coupled, with a low-frequency cutoff of approximately 6 Hz, to signal processor 40, where displacement information is derived, as described above with reference to FIG. 2. In an alternative embodiment, for some applications of the invention, the cosine 68 and sine 70 outputs are DC coupled to successive stages of signal processing. In the preferred embodiment, low frequency processing by signal processor 40 is implemented digitally, though many methods of processing the low-frequency cosine 68 and sine 70 outputs are known in the art.

Figure 4:
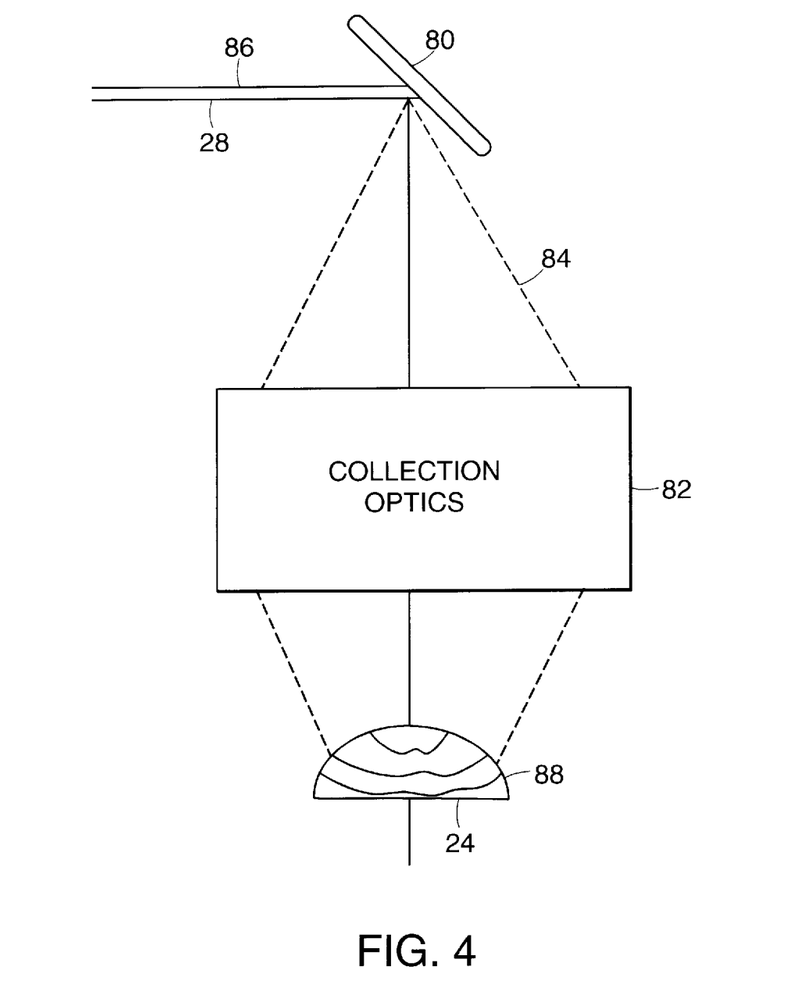
FIG. 4 is schematic view of the operation of a mapping embodiment of the current invention.

In several applications, it is desirable to map the shape of the outer surface of the cornea with great accuracy. This is necessary, for example, to establish the requisite sequence of cuts to be performed in radial keratotomy or to determine if sutures are uniformly stretching the new cornea in cornea transplant surgery, as well as in other refractive procedures and for contact lens fitting. To provide for these applications, an alternative embodiment of the invention, described with reference to FIG. 4, provides for lensed measurement beam 28 to be scanned across the surface of eyeball 24 along paths approximating a series of radial meridians by driving galvanometer scanners 80 such as General Scanning Model G120D, or, alternatively, other scanning means such as acoustooptic deflectors, with a programmed waveform, in a manner known to persons skilled in the art of optical scanning. The scanning may be accomplished by means of a single scanning optical element 80 or, alternatively, by an optical chain incorporating a plurality of components providing for the scanning of radial meridians in a manner known to persons skilled in the art. Successive scans thus provide areal coverage across surface 88 of eyeball 24. Collection optics 82, having a focus substantially coincident with the center of curvature of surface 88 of eyeball 24, provide for the normal incidence of the scanned component 84 of measurement beam 28 relative to surface 88 of eyeball 24, and, similarly, for the substantial coincidence of component 86 of measurement beam 28 reflected by surface 88 of eyeball 24.

Further embodiments within the scope of the invention include incorporation of interferometer 10 in a hand-held unit, as well as a fiber-optic embodiment of interferometer 10 or distinct components of interferometer 10 for implementing the ocular optical heterodyne measurement which is the subject of this invention, such as, for example, the optical configuration for steering measurement beam 20 onto the surface of eyeball 24, or beam splitter 32. The described embodiments of the inventions are intended to be merely exemplary and numerous variations and modifications will be apparent to those skilled in the art. All such variations and modifications are intended to be within the scope of the present invention as defined in the appended claims.

I claim:

1. An optical heterodyne interferometer for measuring precise displacement of an eyeball, comprising:
   an optical configuration for steering a measurement beam onto the surface of the eyeball and receiving a reflected component of the measurement beam from the eyeball;
   a frequency generator having a frequency output;
   a modulator driven by said frequency generator for impressing a frequency shift on at least one of a reference beam and the measurement beam;
   a heterodyne detector, having an input, for producing a heterodyne signal;
   an optical combining means for supplying the reference beam and the reflected component of the measurement beam at the input of said heterodyne detector; and
   a signal processor coupled to the heterodyne detector and to the frequency generator for calculating an ocular displacement based upon the heterodyne signal and the frequency output.

2. An optical heterodyne interferometer as set forth in claim 1, further comprising an optical splitting means for dividing a beam of coherent light into the measurement beam and the reference beam.

3. An optical heterodyne interferometer as set forth in claim 1, further comprising a source of coherent light for producing at least one of the measurement beam and the reference beam.

4. An optical heterodyne interferometer as set forth in claim 1, further comprising an optical means for relaxing the tolerance of alignment between said optical heterodyne interferometer and the eyeball.

5. An optical heterodyne interferometer as set forth in claim 4, wherein said optical means comprises at least one of a beam-defining aperture located in the path of said measurement beam and a lens located in the path of said measurement beam.

6. An optical heterodyne interferometer as set forth in claim 1, further comprising a scanner for mapping said measurement beam at normal incidence across the surface of said eyeball.

7. An optical heterodyne interferometer as set forth in claim 1, wherein said optical configuration for steering the measurement beam onto the surface of the eyeball comprises an optical fiber.

8. An optical heterodyne interferometer as set forth in claim 1, wherein said optical combining means comprises an optical fiber.

9. An optical heterodyne interferometer as set forth in claim 1, further comprising an acoustic generator for directing an acoustic wave having an amplitude toward said eyeball.

10. An optical heterodyne interferometer as set forth in claim 9, further comprising a calculator for deriving an intraocular pressure using said ocular displacement and said amplitude of said acoustic wave.

11. An optical heterodyne interferometer as set forth in claim 1, further comprising an acoustic generator for directing an acoustic wave toward said eyeball collinearly with said measurement beam.

12. An optical heterodyne interferometer as set forth in claim 1, wherein said modulator is an acoustooptic modulator.

13. An optical heterodyne interferometer as set forth in claim 1, further comprising a tracking means for maintaining said measurement beam substantially orthogonal to said surface of the eyeball at the apex of the eyeball.

14. An optical heterodyne interferometer as set forth in claim 1, wherein said signal processor includes a phase detector for detecting a relative phase of the reflected component of the measurement beam with respect to the reference beam.

15. An optical heterodyne interferometer as set forth in claim 14 wherein said phase detector includes a first mixing means for mixing said heterodyne signal with an in-phase component of said frequency output.

16. An optical heterodyne interferometer as set forth in claim 14 wherein said phase detector further includes a plurality of mixing means for mixing said heterodyne signal with a plurality of phase components of said frequency output.

17. An optical heterodyne interferometer as set forth in claim 1 further comprising a scanning means for providing areal coverage of said measurement beam across said eyeball at normal incidence to said eyeball.

18. A method of measuring the displacement of an eyeball comprising the steps of:
   providing a measurement beam of coherent light and a reference beam of coherent light;
   impressing a frequency shift at a modulation frequency on at least one of said reference beam and said measurement beam;
   directing said measurement beam at an eyeball;
   receiving a reflected component of said measurement beam from said eyeball;

heterodyning said reflected component of said measurement beam and said reference beam to produce a heterodyne signal;

processing said heterodyne signal to obtain a displacement of the eyeball.

19. A method of measuring the displacement of an eyeball as set forth in claim 18 wherein said step of processing said heterodyne signal includes the step of mixing said heterodyne signal with said modulation frequency.

20. A method of measuring the displacement of an eyeball as set forth in claim 18 wherein said step of processing said heterodyne signal includes producing an in-phase heterodyne signal and a quadrature heterodyne signal.

21. A method of measuring the displacement of an eyeball as set forth in claim 18 further comprising the step of directing an acoustic wave toward the eyeball.

22. A method of measuring the displacement of an eyeball as set forth in claim 18 further comprising the step of directing an acoustic wave toward the eyeball collinearly with said measurement beam.

23. A method of measuring the displacement of an eyeball as set forth in claim 21 further comprising the step of deriving the intraocular pressure from said displacement of the eyeball and the amplitude of said acoustic wave.

24. A method of measuring the displacement of an eyeball as set forth in claim 21 further comprising the step of correlating said displacement of the eyeball with the amplitude of said acoustic wave.

25. A method of measuring an intraocular pressure comprising the steps of:

providing a measurement beam of coherent light and a reference beam of coherent light;

impressing a frequency shift at a modulation frequency on at least one of said reference beam and said measurement beam;

directing said measurement beam at an eyeball;

receiving a reflected component of said measurement beam from said eyeball;

heterodyning said reflected component of said measurement beam and said reference beam to produce a heterodyne signal;

directing an acoustic wave toward the eyeball;

processing said heterodyne signal to obtain a displacement of the eyeball in response to said acoustic wave; and deriving the intraocular pressure from said displacement of the eyeball.

26. A method of measuring the displacement of an eyeball as set forth in claim 25 wherein said step of directing said acoustic wave includes the step of directing said acoustic wave toward the eyeball collinearly with said measurement beam.

27. A method of measuring the displacement of an eyeball as set forth in claim 25 wherein said step of processing said heterodyne signal includes the step of obtaining a displacement of the eyeball synchronous with said acoustic wave.

28. A method of measuring the displacement of an eyeball as set forth in claim 25 wherein said step of processing said heterodyne signal includes the step of mixing said heterodyne signal with said modulation frequency.

29. A method of measuring the displacement of an eyeball as set forth in claim 25 wherein said step of processing said heterodyne signal includes producing an in-phase heterodyne signal and a quadrature heterodyne signal.

30. An optical heterodyne interferometer for measuring precise displacement of at least one specified point on the surface of an eyeball, the interferometer comprising:

an optical configuration for steering a measurement beam to the at least one specified point on the surface of the eyeball and receiving a reflected component of the measurement beam from the eyeball;

a frequency generator having a frequency output;

a modulator driven by said frequency generator for impressing a frequency shift on at least one of a reference beam and the measurement beam;

a heterodyne detector, having an input, for producing a heterodyne signal having a phase;

an optical combining means for supplying the reference beam and the reflected component of the measurement beam at the input of said heterodyne detector; and a signal processor coupled to the heterodyne detector and to the frequency generator for calculating a displacement of the specified point on the surface of the eyeball relative to a specified reference position based upon the heterodyne signal and the frequency output, the signal processor comprising a phase detector for measuring a magnitude and a sign of the phase of the heterodyne signal relative to a fiducial phase.

31. An optical heterodyne interferometer for measuring precise displacement of at least one specified point on the surface of an eyeball, the interferometer comprising:

an optical configuration for steering a measurement beam to the at least one specified point on the surface of the eyeball and receiving a reflected component of the measurement beam from the eyeball;

a frequency generator having a frequency output;

a modulator driven by said frequency generator for impressing a frequency shift on at least one of a reference beam and the measurement beam;

a heterodyne detector, having an input, for producing a heterodyne signal having a phase;

an optical combining means for supplying the reference beam and the reflected component of the measurement beam at the input of said heterodyne detector; and phase measurement means for calculating a displacement of the specified point on the surface of the eyeball relative to a specified reference position based upon the heterodyne signal and the frequency output.

32. An optical heterodyne interferometer according to claim 1, further comprising:

a display device for depicting a time record of eyeball position versus time.

33. A method for providing a time history of the displacement of a position on the surface of an eyeball, the method comprising:

providing a measurement beam of coherent light and a reference beam of coherent light;

impressing a frequency shift at a modulation frequency on at least one of said reference beam and said measurement beam;

directing said measurement beam at an eyeball;

receiving a reflected component of said measurement beam from said eyeball;

heterodyning said reflected component of said measurement beam and said reference beam to produce a heterodyne signal;

processing said heterodyne signal to obtain a displacement of the eyeball; and displaying the displacement of the eyeball as a function of time.

34. A method of measuring elasto-mechanical properties of an eye comprising the steps of:

providing a measurement beam of coherent light and a reference beam of coherent light;

impressing a frequency shift at a modulation frequency on at least one of said reference beam and said measurement beam;

directing said measurement beam at an eyeball;

applying an acoustic excitation to said eyeball;

receiving a reflected component of said measurement beam from said eyeball;

heterodyning said reflected component of said measurement beam and said reference beam to produce a heterodyne signal;

processing said heterodyne signal to measure a displacement of the eyeball in response to the acoustic excitation; and deriving the elasto-mechanical properties of the eye on the basis of the applied acoustic excitation and the measured displacement of the eyeball.

* * * * *